United States Patent [19]

Warden

[11] Patent Number: 5,713,354
[45] Date of Patent: *Feb. 3, 1998

[54] BIOMAGNETOMETER WITH WHOLE HEAD COVERAGE OF A SEATED RECLINED SUBJECT

[75] Inventor: Laurence Warden, San Diego, Calif.

[73] Assignee: Biomagnetic Technologies, Inc., San Diego, Calif.

[*] Notice: The term of this patent shall not extend beyond the expiration date of Pat. No. 5,471,985.

[21] Appl. No.: 442,578

[22] Filed: May 30, 1995

Related U.S. Application Data

[63] Continuation-in-part of Ser. No. 284,154, Aug. 1, 1994, Pat. No. 5,471,985.

[51] Int. Cl.$^6$ .................................................. A61B 5/05
[52] U.S. Cl. ................................... 128/653.1; 324/248
[58] Field of Search ........................ 128/653.1; 324/244, 324/248

[56] References Cited

U.S. PATENT DOCUMENTS

| | | | |
|---|---|---|---|
| 4,793,355 | 12/1988 | Crum et al. ............................ | 128/653.1 |
| 4,921,198 | 5/1990 | Naser et al. . | |
| 4,951,674 | 8/1990 | Zanakis et al. . | |
| 4,996,479 | 2/1991 | Hoenig . | |
| 5,243,281 | 9/1993 | Ahonen et al. .................... | 128/653.1 X |
| 5,265,611 | 11/1993 | Hoenig et al. .................... | 128/653.1 |
| 5,309,095 | 5/1994 | Ahonen et al. . | |
| 5,339,811 | 8/1994 | Ohta et al. ........................... | 128/653.1 |
| 5,471,985 | 12/1995 | Warden .................................. | 128/653.1 |

FOREIGN PATENT DOCUMENTS

| | | | |
|---|---|---|---|
| 0 554 881 A1 | 8/1993 | European Pat. Off. . | |
| 91-02259 | 2/1991 | WIPO . | |
| 9102259 | 2/1991 | WIPO ................................... | 128/653.1 |

OTHER PUBLICATIONS

T. Ryhanen et al., "SQUID Magnetometers for Low-Frequency Applications", *J. Low Temperature Physics*, vol. 76, Nos. 5/6, pp. 287–290 and 363–369 (1989).

International Standards Organization, "Headforms for use in the testing of protective helmets", ISO Standard 6220 (1983).

Jukka Knuutila et al., "Large-area low-noise seven channel dc SQUID magnetometer for brain research", *Rev. Sci. Instrum.*, vol. 58(11), pp. 2145–2156 (1987).

*Primary Examiner*—Ruth S. Smith
*Attorney, Agent, or Firm*—Gregory Garmong

[57] ABSTRACT

A biomagnetometer includes a dewar vessel having a helmet-shaped recess at the lower end of its body. The recess is angled at about 45 degrees to the dewar body axis of the dewar vessel. Biomagnetic sensors are positioned within the interior of the dewar vessel body around the periphery of the recess. The angled recess permits the biomagnetometer to be used with subjects whose heads are inclined from 0 to 90 degrees to the horizontal by pivoting the dewar vessel over an angle of from −45 degrees to +45 degrees to the vertical, without spilling the cryogenic fluid within the dewar or causing excessive evaporation of the cryogenic fluid.

23 Claims, 5 Drawing Sheets

BIOMAGNETOMETER WITH WHOLE HEAD COVERAGE OF A SEATED RECLINED SUBJECT

BACKGROUND OF THE INVENTION

This application is a continuation-in-part of application Ser. No. 08/284,154, filed Aug. 1, 1994, now U.S. Pat. No. 5,471,985, for which priority is claimed.

This invention relates to the measurement of magnetic fields produced by the brain of a human subject, and, more particularly, to an approach for performing such measurements using an array of sensors surrounding the head of the subject.

The human brain produces electrical signals. These electrical signals are very faint, but they can be measured noninvasively by various approaches. One such technique, biomagnetometry, is based upon the measurement of the magnetic fields produced outside the head of the subject by the electrical current flows of the brain.

A biomagnetometer is a specially adapted, highly sensitive device having a magnetic field sensor, a detector of electrical current flow in the sensor, and associated electronics. The magnetic field sensor is typically a single-loop or multiple-loop coil of wire which produces a small current flow when a magnetic flux penetrates the loop. The sensor is desirably placed as closely as possible to the head of the subject whose brain signals are to be measured, because the strength of the magnetic field decreases rapidly with distance from the source. The detector is typically a superconducting quantum interference device ("SQUID"), which can detect very small electrical currents.

The sensor and the detector are made of superconducting materials. They are operated at very low temperatures in order to attain their superconducting states and also to suppress noise sources that increase with increasing temperature. Currently available sensor/detector elements are operated at liquid helium temperature, about 4.2° K. In order to be maintained at this temperature, the sensor and detector are placed into an insulating vessel termed a dewar, and cooled with liquid helium. A typical dewar is about 24 inches in diameter and 48 inches in length. The size of the dewar and the need to place the sensors as closely as possible to the head of the subject dictate careful geometric design of the dewar. In the usual practice, the sensors are placed into a small-diameter extension of the main dewar vessel, termed a dewar tail, that can be positioned closely to the head of the subject.

The preceding discussion has described a single measurement channel having a single sensor and its associated single detector. The earliest biomagnetometers were built around a single measurement channel, but later designs have incorporated multiple measurement channels into a single unit. Current biomagnetometers have tens of measurement channels, and future instruments may have even more.

An important trend in the advance of biomagnetometry is the development of a capability for full-head coverage of subjects. That is, the sensors may be arranged in an array that is positioned around the head of the subject. The magnetic fields produced by the brain of the subject are measured by all of the sensors simultaneously. The measurements are analyzed to determine the position and strength of the source or sources within the brain.

Various methods for positioning, cooling, and supporting the full-head array of sensors have been proposed. In one, the lower end of the dewar is shaped in the manner of a helmet that fits over a portion of the entire head of the patient. The subject sits fully upright in a chair, and the dewar is lowered over the head of the subject until as close a fit as possible is attained. The sensors are immersed in a liquid helium reservoir inside the dewar and positioned about the inner surface of the helmet-shaped recess. By this approach, the well-known technology of existing biomagnetometers is used with a specialized configuration of the lower end of the dewar in order to perform full-head measurements of the subject.

The present inventor has recognized that, while such an approach is operable and useful, it also has shortcomings. Perhaps most importantly, the presently proposed biomagnetometers having full-head coverage are operable only when the subject is sitting in a rigidly defined upright position. Many subjects cannot be presented in an upright position due to their illnesses or infirmities. In one important application, the subject may be a candidate for surgery that is to be performed with the patient in a reclining position. The biomagnetic measurements are used to aid the neurosurgeon in planning the surgery, which must be conducted very precisely in order that vital areas of the brain not be damaged. A measurement performed on the sitting subject may not be applicable for certain surgical procedures undertaken with the patient reclined because of a slight shifting of the location of the brain that is known to occur between the sitting and the reclining positions. Thus, it is highly desirable to perform the biomagnetic measurements with the subject in the reclining position for this particular application.

The dewar containing the sensors cannot be arbitrarily positioned at any desired angle in order to fit the helmet-shaped recess over the head of the subject, because the dewar contains liquefied gas that can shift to expose otherwise-submerged detectors or even spill if the dewar is tilted at too steep an angle. A high tilt angle of the dewar can also expose and effectively short thermal pathways, resulting in a high evaporation rate of the liquefied gas. One solution to the problem of performing full-head measurements is to supply two dewars, one for sitting and one for reclining subjects. This approach is expensive and not fully satisfactory, because it may be desirable to position the subject at an intermediate position between upright and reclining positions. Various types of dewars with movable lower ends can also be envisioned, but these designs are complex, are subject to leaks, are heavy, and are not readily realizable with currently available materials.

There is a need for an improved approach to performing full-head biomagnetic measurements of a subject. The present invention fulfills this need, and further provides related advantages.

SUMMARY OF THE INVENTION

The present invention provides a full-head coverage biomagnetometer operable with the subject in a fully upright, fully reclined, or intermediate position. A single dewar having a fixed construction is used. Known techniques of dewar wall fabrication and other manufacturing procedures are employed to minimize the chances of leakage and to utilize existing design-optimization practices.

In accordance with the invention, an apparatus for performing biomagnetic measurements comprises a dewar vessel, an array of biomagnetic sensors within the dewar, and means for detecting signals produced by the biomagnetic sensors. The dewar vessel comprises an insulated, liquid-tight, elongated hollow body having a dewar body axis parallel to a direction of elongation of the dewar body.

The dewar vessel also includes a recess surface having a recess surface cranial portion substantially in the shape of a headform cranial portion of a human headform. The headform is defined by a generally cylindrical surface having a headform reference axis coincident with the cylindrical axis and is further defined by the headform cranial portion configured to embrace the human cranium and having a headform cranial periphery continuous with the generally cylindrical surface. The recess surface is oriented such that the headform reference axis is at an angle to the dewar body axis of from about 20 degrees to about 60 degrees, most preferably about 45 degrees. The array of biomagnetic sensors is positioned around at least a portion of the periphery of the recess surface.

Alternatively, the recess may be described as an elongated recess in an external surface of the hollow body. The recess is sized sufficiently large to receive a human head therein such that the forehead, cranial, temporal and occipital regions of the head are received therein. The recess has a recess axis parallel to the direction of elongation of the recess. The recess axis is oriented at from about 20 to about 60 degrees to the dewar body axis.

The sensor array is preferably positioned closely adjacent to the inner surface of the recess, so that the sensor array is inclined at the same angle as the recess. The recessed, helmet-like wall of the dewar body is placed over the head of the subject to provide full-head sensor coverage.

The recess and the sensor array are oriented at an angle of from about 20 to about 60 degrees to the dewar body axis. The most preferred angular relation is 45 degrees. With this most preferred construction, the dewar vessel is pivoted about an axis in a horizontal plane at an angle of about −45 degrees to the vertical to accommodate a subject sitting in the fully upright position. In this orientation, the recess and sensor array open downwardly and receive the head of the upright subject. To accommodate a fully reclining (horizontal) subject, the dewar is pivoted about the same axis to an angle of about +45 degrees to the vertical. In this orientation, the recess and sensor array open horizontally, and receive the head of the reclining subject. Tests have shown that conventional dewars can be readily pivoted using a dewar support system between the −45 and +45 degree positions without damage to the dewar. An important virtue of the present design and approach is that it also accommodates any intermediate position of the head of the subject between the upright and reclining positions, by adjusting the pivoting position of the dewar. For some neurosurgery, for example, it may be preferred that the patient be placed in such an intermediate position for best access by the neurosurgeon.

The present invention provides an important advance in the art of biomagnetometry, and specifically full-head coverage for measurements of activity within the brain of the subject. It is noted that various types of stand-alone helmet configurations for biomagnetic monitors have been proposed. Such designs do not operate in conjunction with a conventional dewar, but instead simply sit on the head of the user. However, at the present time most of these stand-alone helmet designs are not readily implemented for a variety of reasons, and in any event helmet designs may never be able to achieve the very low sensor temperatures required to realize the greatest sensitivity. The present approach provides a biomagnetometer design that is implemented in conjunction with known dewar cooling technology and that can achieve liquid helium temperatures in the sensors and detectors of the system.

Other features and advantages of the present invention will be apparent from the following more detailed description of the preferred embodiment, taken in conjunction with the accompanying drawings, which illustrate, by way of example, the principles of the invention.

DETAILED DESCRIPTION OF THE INVENTION

Figure 1:
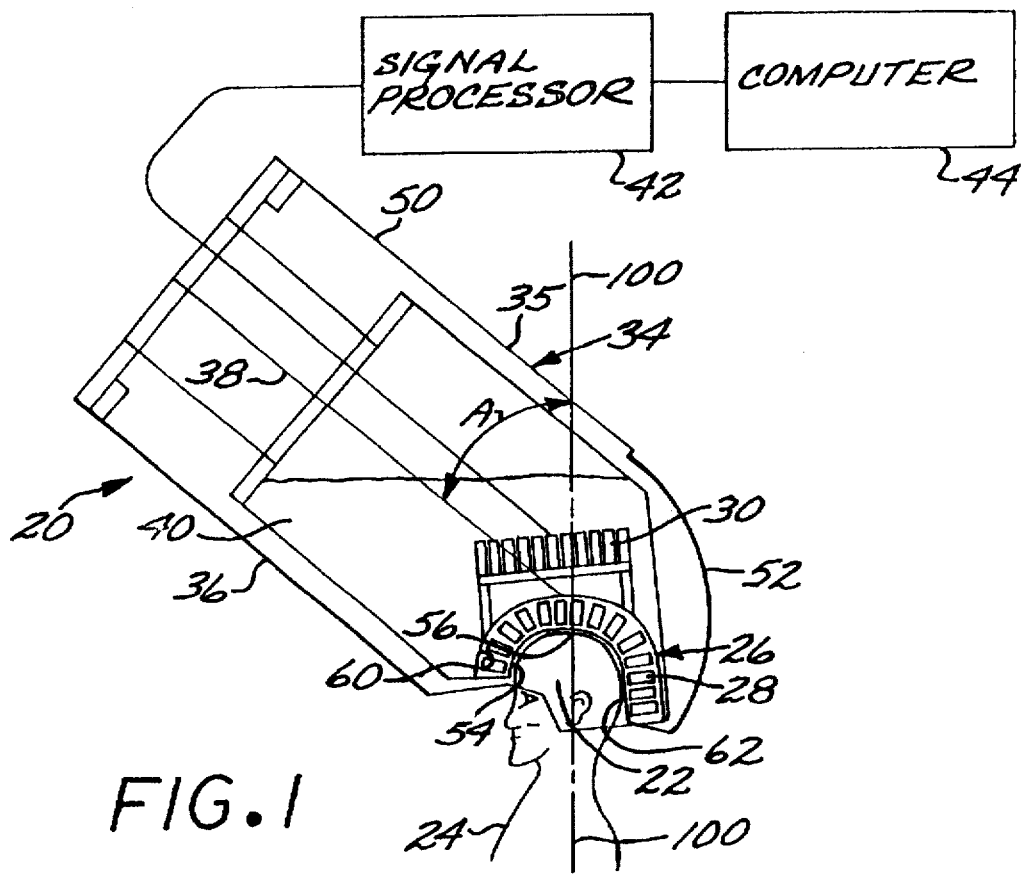
FIG. 1 is a schematic side sectional view of the apparatus of the invention used with a subject in a fully upright sitting position, and including the electronics used in signal analysis.

The present invention is embodied in a biomagnetometer apparatus 20 for obtaining biomagnetic data from a head 22 of a human subject 24. The apparatus 20 includes an array 26 of magnetic field sensors in the form of pickup coils 28 for measuring small magnetic fields. The pickup coils 28 may be magnetometers or gradiometers, or of other configuration as may be appropriate for a particular application. The geometry and orientation of the array 26 of magnetic field pickup coils will be discussed subsequently.

The output signal of each magnetic field pickup coil 28 is detected by a detector, preferably a superconducting quantum interference device 30 ("SQUID"). There is typically one SQUID 30 for each pickup coil 28. These components, together with the associated electronics, form a single channel. A typical apparatus 20 may have tens of channels.

Both the magnetic field pickup coil 28 and the SQUID 30 are maintained at a cryogenic operating temperature within a vacuum-insulated dewar vessel 34 that has a vacuum-supporting wall and appropriate insulation. An outer wall 35 of the dewar vessel 34 functions as its external body 36, which can be described as having a dewar body axis 38. In a preferred form, an upper portion of the body 36 is cylindrical with a diameter of about 24 inches and a length (in the cylindrical portion) of about 48 inches. The dewar body axis 38 is coincident with the cylindrical axis of the cylindrical portion of the dewar body 36 in this case. The dewar body 36 functions as an insulated vessel that contains a cryogenic liquid 40. The required type of cryogenic liquid 40 is determined in part by the cooling requirements of the SQUID. In most instances, measurements of signals produced by the brain require a low temperature to suppress temperature-dependent noise, and liquid helium is used as the cryogenic liquid. The present approach is also operable in conjunction with advanced dewar designs in which the pickup coils and/or SQUIDs are supported in a vacuum rather than immersed in the cryogenic liquid.

The electronics arrangement of the apparatus 20 is illustrated schematically in FIG. 1. The magnetic signals from the brain are sensed by the magnetic field pickup coil 28, which produces a small electrical current output signal when penetrated by magnetic flux. The output signal of the pickup coil 28 is detected by the detector, in this case the SQUID 30. The SQUID 30 produces an electrical voltage proportional to the magnetic flux detected by the pickup coil. The output signal of the SQUID 30 is processed in an ambient-temperature electronic signal processor 42, which typically includes balancing, gain, amplifying, and filtering circuitry, and stored and analyzed in a computer 44 as a function of time. Each sensor channel results in a record of its response to the magnetic field produced by all of the sources within the subject brain, as those sources act simultaneously on the pickup coil of the sensor channel. For simplicity, FIG. 1 depicts only a single sensor channel including a pickup coil and a SQUID, but in practice there is typically a signal processor 42 for each of the SQUID 30/pickup coil 28 sets.

The apparatus 20 and the subject 24 are preferably, but not necessarily, enclosed within a magnetically shielded room 46, also termed an MSR, that shields the apparatus from external influences. The MSR 46 is shown schematically in FIGS. 3 and 4. By screening off the external influences, the amount of signal processing and tiketing required to obtain a meaningful indication of the biomagnetic field are reduced. The signal processor 42 and computer 44 are typically located outside the MSR 46, so that they do not interfere with the sensing of the magnetic field of the subject.

The basic structure of some components of this system are known. The construction of vacuum enclosures is disclosed in U.S. Pat. No. 4,773,952. The construction and operation of magnetic field sensors, including pickup coils, SQUIDs, and ambient-temperature SQUID electronics are disclosed in U.S. Pat. Nos. 3,980,076; 4,079,730; 4,386,361; and 4,403,189. A biomagnetometer is disclosed in U.S. Pat. No. 4,793,355. Magnetically shielded rooms are disclosed in U.S. Pat. Nos. 3,557,777 and 5,043,529. The disclosures of all of these patents are incorporated herein by reference.

As shown in FIG. 1, the pickup coils 28 are arranged in the helmet-shaped array 26 that is contained within the wall 35. In the preferred embodiment, an upper portion 50 of the wall 35 is cylindrical. A lower portion 52 of the wall 35 is shaped to include a helmet-shaped recess 54 that is sized to receive the head 22 of the subject 24 therein. It is desirable that the pickup coils 28 be as close as possible to the magnetic field source within the brain of the subject 24. The helmet-shaped recess 54 in the wall 35 is therefore cooperatively structured with the array 26 of pickup coils 28, so that the individual pickup coils 28 are positioned closely adjacent to the interior wall of the helmet-shaped recess 54.

Figure 6:
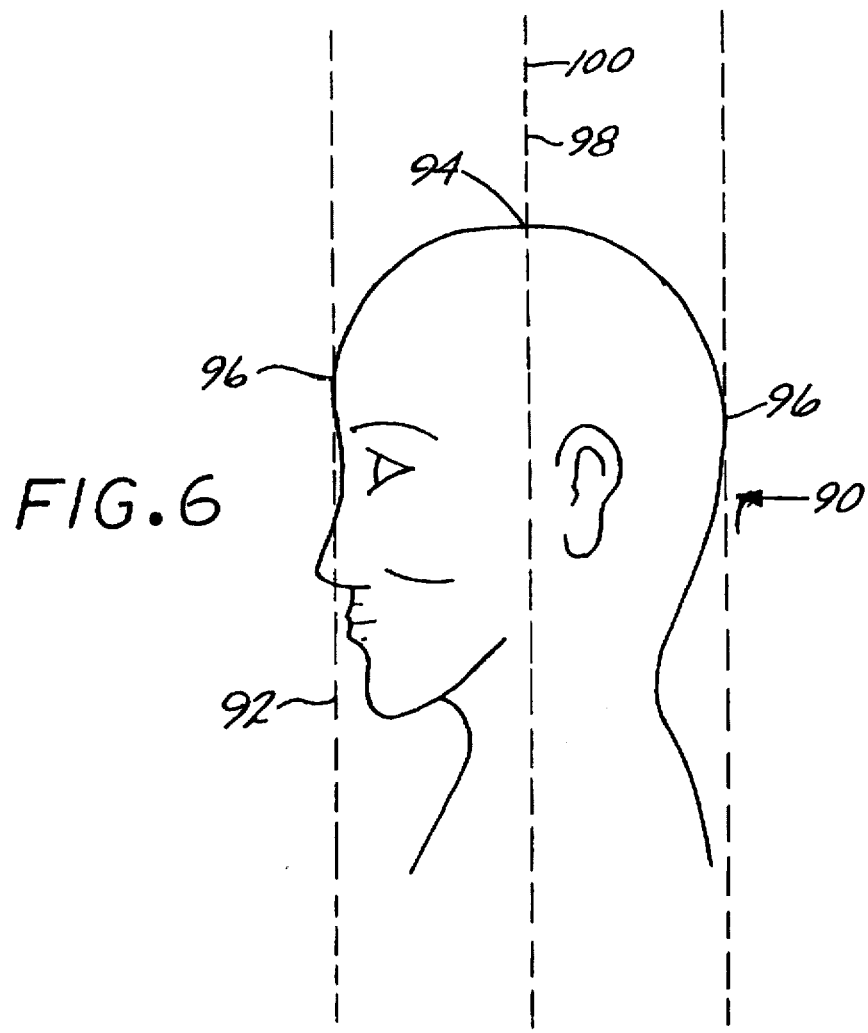
FIG. 6 is a schematic diagram of a frame of reference for analyzing the apparatus of the invention.

The surface of the recess 54 is substantially in the shape of a headform cranial portion of a human headform. FIG. 6 depicts a set of reference relations that are useful in defining the orientation of the recess. The recess is shaped to conform to a portion of the human head, and is also oriented so that the angle of the recess to the dewar body axis 38 is from about 20 to about 60 degrees. The human head is not of a shape that is easily defined by a single standard form. Various techniques have been employed to define the headform in a general sense. In one such technique, the headform is defined as a cylinder that approximately conforms to the lower part of the head, topped by a curved headform cranial portion. This technique has been utilized, for example, by the International Standards Organization (ISO) in setting standards for testing of protective helmets, see ISO Recommendation R1511 and Draft International Standard ISO/DIS 6220. See also U.S. Pat. No. 5,309,095. The disclosures of these publications are incorporated by reference.

Figure 4:
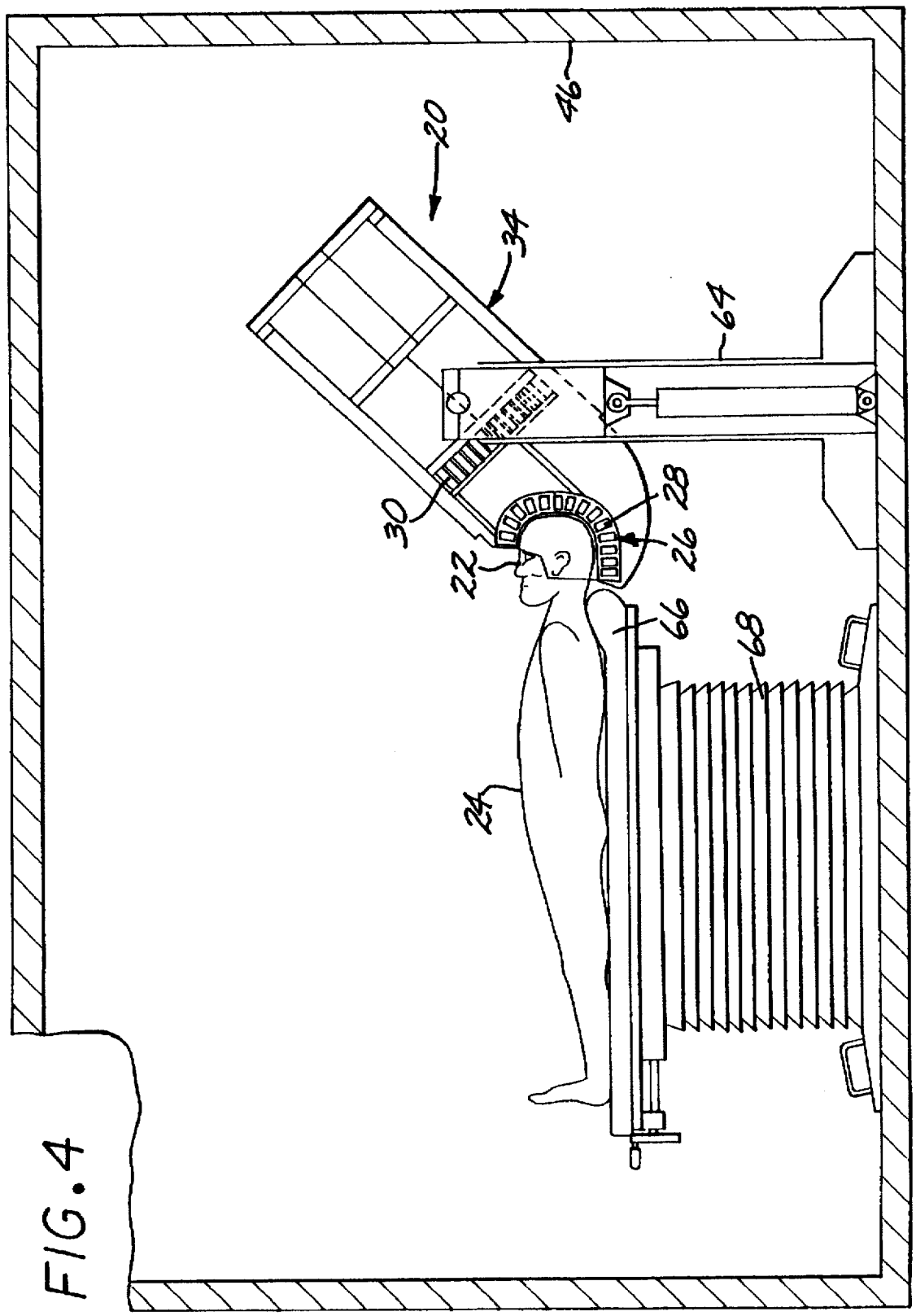
FIG. 4 is an elevational view of the apparatus of the invention used with a subject in a fully reclining position, within a magnetically shielded room that is shown in schematic section.

These approaches both utilize a cylindrical headform portion that defines a headform axis (e.g., axis Z in FIG. 4 of the '095 patent). The approaches differ in that the headform cranial portion is defined empirically in the ISO publications and by a set of intersecting hemispheres and cones in the '095 patent.

For the purposes of the present invention, it is necessary to establish the reference axis for the headform. Referring to FIG. 6, the headform 90 is defined by a generally cylindrical surface 92 and a curved headform cranial portion 94 that is continuous with the cylindrical surface 92. As used herein, the term "generally cylindrical" refers to a surface formed by moving a planar curve along an axis, termed the "cylindrical axis", that lies perpendicular to the plane in which the curve lies. The generally cylindrical surface therefore has the characteristics of a right-circular cylinder, except that the cross section is the planar curve, not a circle.

Preferably, a headform cranial portion periphery 96 is tangent to the generally cylindrical surface 92. The generally cylindrical surface 92 has a cylindrical axis 98. A headform reference axis 100 is coincident with the cylindrical axis 98. The generally cylindrical surface 92 has a size such that the headform is inscribed therein. The shape of the headform cranial portion is such as to embrace the human cranium, including the forehead, cranial, temporal, and occipital regions. For standardization purposes, it is described either empirically (as in the ISO standards) or by a set of approximate geometrical figures (as in the '095 patent). Either standardized approach, or any other operable approach, may be used to define the shape of the headform cranial portion 94.

The recess 54 is shaped to conform to at least a portion of the headform 90, and in particular to the headform cranial portion 94. The recess 54 is oriented such that the headform reference axis intersects the dewar body axis 38 at an angle of from about 20 to about 60 degrees, most preferably at an angle of 45 degrees. If the angle between the headform reference axis 100 and the dewar body axis 38 is less than about 20 degrees or more than about 60 degrees, the dewar cannot accommodate the range of movement of the positions of the head of the subject without requiring excessively large tilting of the dewar vessel 34. Such excessively large tilting may cause the cryogenic liquid in the vessel to spill or may expose the cooled elements within the vessel to result in greatly reduced thermal efficiency. The invention of the parent application Ser. No. 08/284,154 was premised on the use of a fully supine body position for those subjects with serious illnesses or infirmities. Accordingly, the minimum angle between the headform reference axis 100 and the dewar body axis 38 was determined to be about 30 degrees. Further studies have shown that many subjects can tolerate an inclination of up to about 10 degrees above supine, an angle corresponding to the position of the subject's head resting on a pillow, without adverse effects on either the subject or the recorded data. (Biomagnetic data from the brain varies according to the angle of inclination of the subject.) For these cases, the minimum angle between the headform reference axis 100 and the dewar body axis 38 is therefore about 20 degrees, although the preferred minimum angle between the headform reference axis 100 and the dewar body axis 38 is about 30 degrees in order to accommodate fully supine subjects.

From an apex 56 of the recess 54 and the headform 90, through which the headform reference axis 100 passes, the wall of the recess 54 extends both outwardly (relative to the interior of the vessel 34) and to the left in the view of FIG. 1, and outwardly and to the right. The preferred structure for the recess is to cover the forehead of the subject on one side, and to cover the lower part of the head (occipital region) extending to the upper vertebrae of the spine on the other side. To state the distances involved in a preferred embodiment, it is observed that the dewar body axis 38 and the headform reference axis 100 define a pivoting plane. The section of FIG. 1 is made in that pivoting plane. The wall of the recess 54 includes a concavely curved (relative to the interior of the vessel 34) recess wall first segment 60 that extends outwardly from the inwardly extending point by a distance of from about 2½ to about 3½ inches as measured parallel to the headform reference axis 100, and to the left (as viewed in FIG. 1) a distance of from about 4 to about 4½ inches as measured in the pivoting plane and perpendicular to the headform reference axis 100. The wall of the recess 54 includes a concavely curved recess wall second segment 62 that extends outwardly from the inwardly extending point by a distance of from about 7 to about 8 inches as measured parallel to the headform reference axis 100, and to the right (as viewed in FIG. 1) a distance of from about 4 to about 4½ inches as measured in the pivoting plane and perpendicular to the headform reference axis 100. The recess of these dimensions, and a width of about 7 inches (measured perpendicular to the pivoting plane) provides full-head coverage for most persons. Other magnetic field pickup coils and their associated detectors are positioned on the sides of the helmet-shaped recess, out of the plane of view of FIG. 1.

Figure 2:
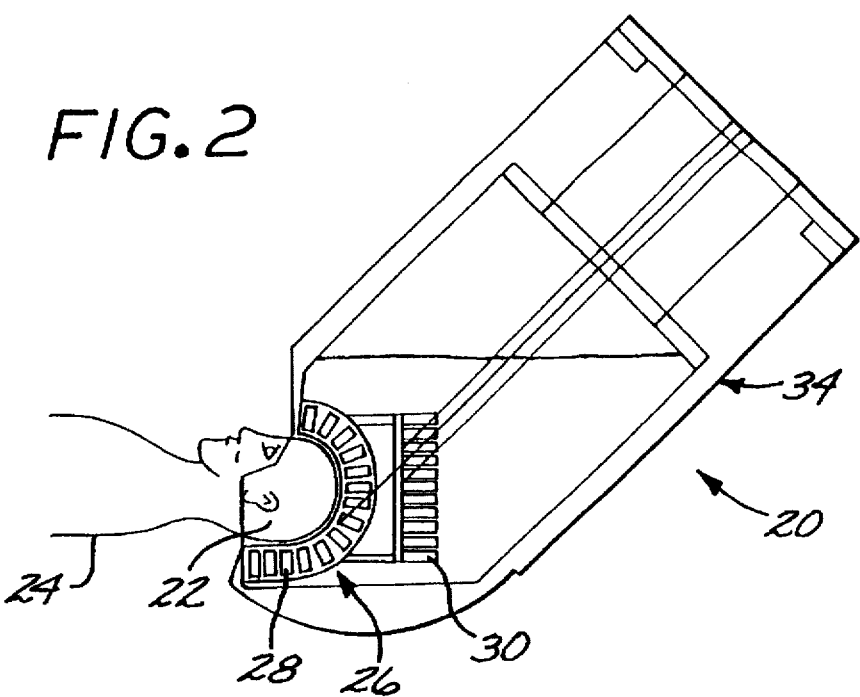
FIG. 2 is a schematic side sectional view of the apparatus of the invention used with a subject in a fully reclining position.

This angled arrangement of the recess 54 permits the apparatus 20 to be used without structural modification for the subject 24 in both the upright seated position shown in FIG. 1 and the fully reclined position shown in FIG. 2. To accomplish this multipositional use, the dewar vessel 34 is rotated in the pivoting plane (defined by the intersecting dewar body axis 38 and headform reference axis 100). At a position wherein the dewar body axis 38 is rotated −45 degrees from vertical, as shown in FIG. 1, the recess 54 opens vertically downwardly to accommodate the subject 24 sitting fully upright. At a position wherein the dewar body axis is rotated +45 degrees from vertical, as shown in FIG. 2, the recess 54 opens horizontally (to the left in FIG. 2) to accommodate the subject 24 in a fully reclined position. The rotations of −45 degrees and +45 degrees do not cause spillage of the cryogenic liquid 40, exposure of the SQUIDs 30 above the surface of the cryogenic liquid, excessively reduced thermal efficiency, or any other damage.

Figure 3:
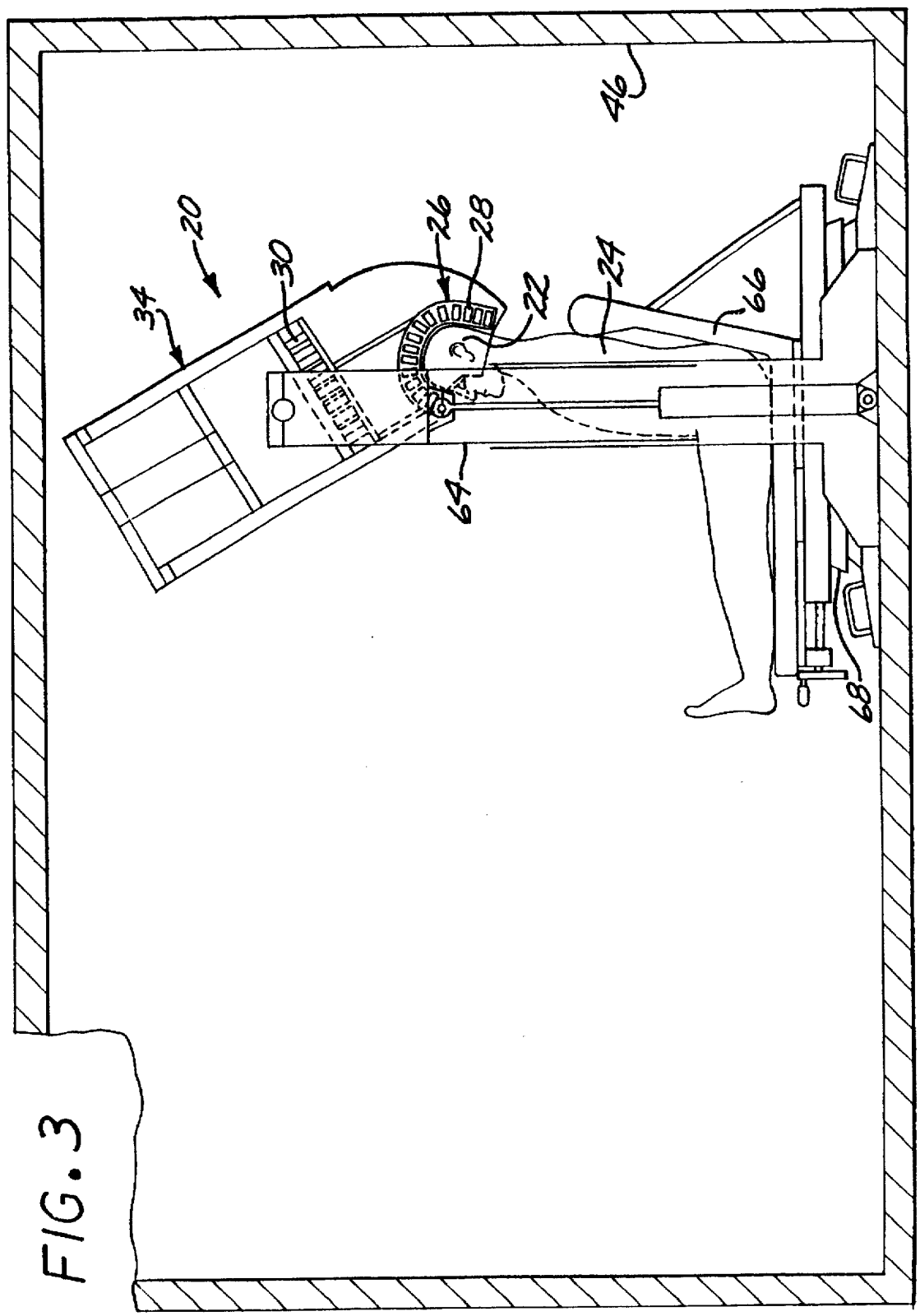
FIG. 3 is an elevational view of the apparatus of the invention used with a subject in a position intermediate between fully upright sitting and fully reclining, within a magnetically shielded room that is shown in schematic section.

As shown in FIG. 3, the dewar vessel 34 is pivotably supported in a support stand 64 that permits the dewar vessel 34 to be pivoted from the −45 degree position to the +45 degree position in the pivoting plane. The subject 24 rests on a subject support 66 that is illustrated as a segmented pad whose upper end can be pivoted upwardly. The subject support 66 is raised or lowered by any operable approach, here illustrated as a pneumatic bed 68.

A particular advantage of the approach of the invention is that it accommodates the subject when sitting fully upright or fully reclining, and also any intermediate position. The fully upright position is not comfortable for some persons, so a nearly fully upright, but slightly reclined position such as illustrated in FIG. 3 can be used. The recess 54 of the dewar vessel 34 is readily positioned to receive the head of the subject simply by changing the pivot angle from −45 degrees to a lesser angle that is reduced from −45 degrees by the amount of the angle of the reclining of the head from the vertical.

To use the apparatus 20 with the subject in the reclining position (FIG. 4) after it has been used in the sitting position (FIGS. 1 or 3), the support stand 64 and its dewar vessel 34 are moved away. The subject support 66 is dropped to the horizontal position, and the pneumatic bed 68 is raised. The dewar vessel 34 is pivoted to the +45 degree position. The support stand 64 is then moved into place with the helmet-shaped recess 54 over the head of the subject, as shown in FIG. 4. (The measurement with the subject in the sitting position, FIGS. 1 or 3, is ordinarily accomplished with the pneumatic bed 68 as low as possible in order to provide overhead clearance for the dewar vessel 34 inside the ceiling of the MSR 46.)

Figure 5:
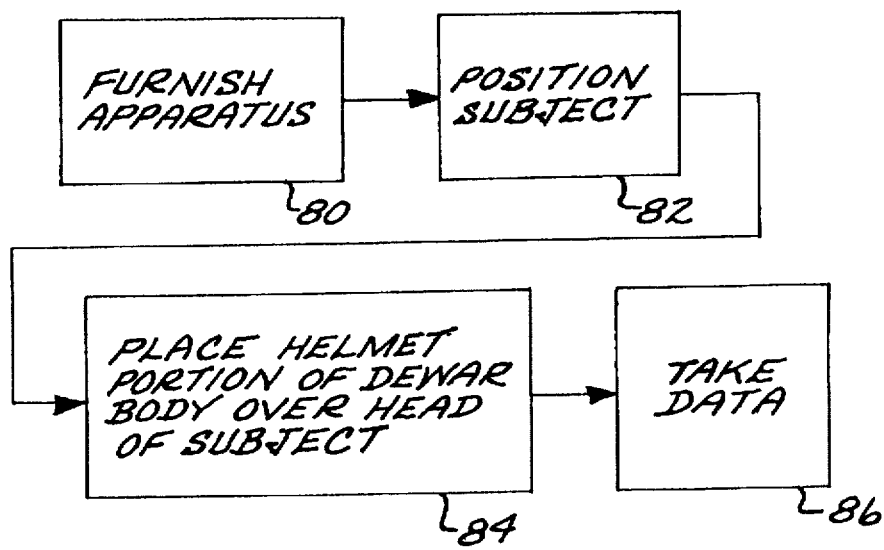
FIG. 5 is a block flow diagram for the method according to the invention.

FIG. 5 depicts a method for performing biomagnetic measurements. The apparatus 20 as described above is furnished, numeral 80. The subject is positioned, numeral 82. The dewar vessel is positioned to permit the head of the subject to be received within the helmet-shaped recess, and the head of the subject is so placed, numeral 84. Biomagnetic measurements are taken, numeral 86, typically using data from the entire array of pickup coils extending around the head of the subject. The steps 82, 84, and 86 can be repeated as necessary with the subject in other positions, as described above in relation to FIGS. 3 and 4.

Figure 7:
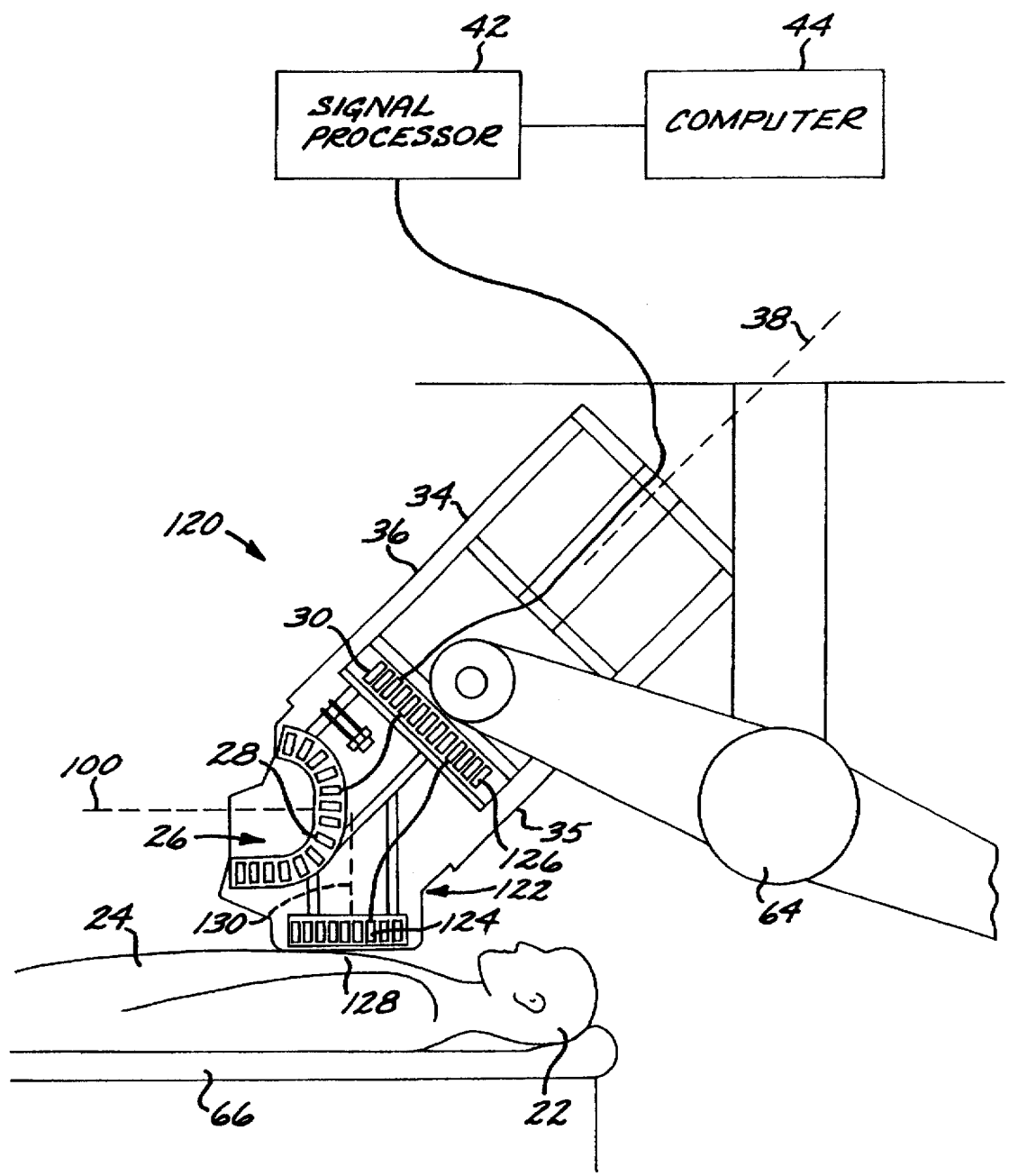
FIG. 7 is a side sectional view of a second embodiment of the invention.

Another embodiment of the invention is illustrated in FIG. 7 as the apparatus 120. Many of the elements of the apparatus 120 are substantially the same as the correspondingly numbered elements in the apparatus 20. In those cases the same reference numerals are utilized in relation to the apparatus 120, and the prior description of the elements is incorporated herein.

The embodiment of FIG. 7 provides the capability for measuring biomagnetic signals from the head using the approach previously described, and the capability for measuring biomagnetic signals from other parts of the body and in particular from the heart of the subject located in the chest region. In the embodiment 120, the wall 35 of the dewar vessel 34 is modified so as to accommodate a second array of sensors 122 including a number of pickup coils 124 and associated SQUIDs 126. The pickup coils 124 are preferably positioned in a generally planar arrangement, although the array of pickup coils 124 may be slightly concave about one axis so as to be shaped to the convex shape of a chest 128 of the subject 24. The wall 35 of the dewar vessel 34 in the region of the pickup coils 124 is shaped to the same shape as the array of pickup coils, so that the pickup coils 124 are closely adjacent to the inside surface of the wall 35.

The orientation of the second array 122 is defined by a second array axis 130, which is perpendicular to the plane of the planar array of pickup coils 124 in the preferred form of this embodiment. The second array axis is preferably oriented at 90° to the headform reference axis. In the apparatus 120, it is preferred that the angle between the headform reference axis 100 and the body axis 38 be 45°, although other angles are operable. Consequently, in this preferred fonu the second array axis 130 is oriented at 45° to the body axis 38. This arrangement produces a convenient arrangement for the two sets of pickup coils 28 and 124, which are perpendicular to each other and therefore well separated and remote from each other so that they do not physically interfere.

The array 26 is used for measurements of signals produced by the brain, as discussed previously. The second array of sensors 122 is used for measurements of other parts of the body, and typically for measurements of the heart of the subject. FIG. 7 shows the second array 122 located adjacent to the chest 128 of the subject to measure the heart. To measure the brain signals of the subject in the fully reclined position, the subject or the dewar assembly is translated so that the first sensor array 26 fits over the head of the subject, as was illustrated in FIG. 4. Measurements of the brain signals of the subject in the partially or fully upright position are accomplished by tilting the dewar as illustrated in FIG. 3. The heart signals of the patient in the partially or fully upright position can be measured by translating the dewar from the location shown in FIG. 3 so that the second array is positioned adjacent the chest of the subject.

The pickup coils 124 function is substantially the same manner as the pickup coils 28, except for the positioning so as to be useful in measuring signals from the chest of the subject. Preferably, one SQUID 126 is provided for each of the pickup coils 28, and the output signals of the SQUIDs 126 are provided to the same signal processor 42 and computer 44 as used for the array 26. The array 26 and the second array 122 do not typically operate at the same time, and it is therefore possible to multiplex signals from the pickup coils 28 and 124 to a single set of SQUIDs, or to multiplex signals from the SQUIDs to the signal processor 24. See, for example, the approach described in allowed application Ser. No. 08/248,533, whose disclosure is incorporated by reference.

The embodiment of FIG. 7 has the particular advantage that it is necessary to employ only a single instrument for measurements of the head and the torso of a subject, in any position ranging from fully reclining to fully upright. Costs and availability of apparatus for making biomagnetic measurements are thereby substantially improved. The placement of the array 26 at an angle to the body axis 38 permits the second array 122 to be built into the same dewar body 36 and used for torso measurements.

The present invention provides an advance in the utilization of the potential of full-head coverage biomagnetic measurements. A single apparatus can be used to accomplish full-head measurements without hardware reconfiguration other than a simple tilting of the dewar vessel. Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. Apparatus for performing biomagnetic measurements, comprising:

a dewar vessel comprising
   an insulated, liquid-tight, elongated hollow body with an outer wall having an upper portion and a lower portion, and a dewar body axis parallel to a direction of elongation of the body, and
   an elongated recess in the lower portion of the outer wall and extending toward an interior of the hollow body, the recess being shaped to embrace the forehead, cranial, temporal, and occipital regions of the human cranium and comprising a generally cylindrical surface with a cylindrical axis, and further comprising a cap surface continuous with the generally cylindrical surface, the cylindrical axis of the generally cylindrical surface being oriented at an angle to the dewar body axis of from about 20 degrees to about 60 degrees;
 an array of biomagnetic sensors within the dewar body and positioned around at least a portion of the periphery of the recess surface; and
 means for detecting signals produced by the biomagnetic sensors.

2. The apparatus of claim 1, wherein the hollow body is substantially cylindrical in shape.

3. The apparatus of claim 1, wherein the array of sensors includes a plurality of magnetic field pickup coils and the means for detecting includes a plurality of superconducting quantum interference devices, each pickup coil having a superconducting quantum interference device in electrical communication therewith.

4. The apparatus of claim 1, further including
 means for supporting the dewar vessel and for pivoting the dewar vessel about a horizontal axis through an angle of from about −45 degrees relative to a vertical axis to about +45 degrees relative to the vertical axis.

5. The apparatus of claim 1, further including
 means for supporting a head of a patient at an angle to a horizontal plane of from zero to 90 degrees.

6. The apparatus of claim 1, further including
 a second array of biomagnetic sensors within the dewar body positioned remotely from the array of biomagnetic sensors.

7. The apparatus of claim 6, wherein the second array of biomagnetic sensors is substantially planar.

8. The apparatus of claim 6, wherein the recess axis is oriented at an angle of 45 degrees to the dewar body axis, and wherein the second array of biomagnetic sensors is oriented at an angle of about 45 degrees to the dewar body axis and at an angle of about 90 degrees to the recess axis.

9. The apparatus of claim 1, wherein at least some of the biomagnetic sensors are positioned in a facing relationship with the cap surface of the elongated recess and at least some of the biomagnetic sensors are positioned in a facing relationship with the cylindrical portion of the elongated recess.

10. The apparatus of claim 1, wherein the array of biomagnetic sensors is in a vacuum.

11. The apparatus of claim 1, wherein the array of biomagnetic sensors is immersed in a cryogenic liquid.

12. Apparatus for performing biomagnetic measurements, comprising:

a dewar vessel comprising
   an insulated, liquid-tight, elongated hollow body, the elongated hollow body having a dewar body axis parallel to the direction of elongation of the body, and
   an elongated recess in an external surface of the hollow body, the recess being sized sufficiently large to receive a human head therein such that the forehead, cranial, and occipital regions of the head are received therein, the recess having a recess axis parallel to the direction of elongation of the recess, the recess axis being oriented at an angle of from about 20 to about 60 degrees to the dewar body axis;
 an array of biomagnetic sensors within the dewar body and positioned around at least a portion of the periphery of an internal surface of the recess;
 means for detecting signals produced by the biomagnetic sensors; and
 a second array of biomagnetic sensors within the dewar body positioned remotely from the array of biomagnetic sensors, wherein the second array of biomagnetic sensors is substantially planar.

13. The apparatus of claim 12, wherein the recess axis is oriented at an angle of about 45 degrees to the dewar body axis.

14. The apparatus of claim 12, wherein the hollow body is substantially cylindrical in shape.

15. The apparatus of claim 12, wherein the array of sensors includes a plurality of magnetic field pickup coils and the means for detecting includes a plurality of superconducting quantum interference devices, each pickup coil having a superconducting quantum interference device in electrical communication therewith.

16. The apparatus of claim 12, further including
means for supporting the dewar vessel and for pivoting the dewar vessel about a horizontal axis through an angle of from about −45 degrees relative to a vertical axis to about +45 degrees relative to the vertical axis.

17. The apparatus of claim 12, further including
means for supporting a head of a patient at an angle to a horizontal plane of from zero to 90 degrees.

18. The apparatus of claim 12, wherein at least some of the biomagnetic sensors are positioned in a facing relationship with a portion of the recess that receives the cranial region of the head and at least some of the biomagnetic sensors are positioned in a facing relationship with a portion of the recess that receives the occipital region of the head.

19. The apparatus of claim 12, wherein the array of biomagnetic sensors is in a vacuum.

20. The apparatus of claim 12, wherein the array of biomagnetic sensors is immersed in a cryogenic liquid.

21. Apparatus for performing biomagnetic measurements, comprising:
a dewar vessel comprising
an insulated, liquid-tight, elongated hollow body, the elongated hollow body having a dewar body axis parallel to the direction of elongation of the body, and
an elongated recess in an external surface of the hollow body, the recess being sized sufficiently large to receive a human head therein such that the forehead, cranial, and occipital regions of the head are received therein, the recess having a recess axis parallel to the direction of elongation of the recess, wherein the recess axis is oriented at an angle of 45 degrees to the dewar body axis
an array of biomagnetic sensors within the dewar body and positioned around at least a portion of the periphery of an internal surface of the recess;
means for detecting signals produced by the biomagnetic sensors; and
a second array of biomagnetic sensors within the dewar body positioned remotely from the array of biomagnetic sensors, wherein the second array of biomagnetic sensors is oriented at an angle of about 45 degrees to the dewar body axis and at an angle of about 90 degrees to the recess axis.

22. A method of measuring biomagnetic signals produced by a human head, comprising the steps of
furnishing an apparatus comprising
an insulated, liquid-tight, elongated hollow dewar body with an outer wall having an upper portion and a lower portion, and a dewar body axis parallel to a direction of elongation of the body, and
a recess surface in the lower portion of the outer wall and extending toward an interior of the dewar body substantially in the shape of a human headform, the recess surface comprising a generally cylindrical surface with a cylindrical axis and further comprising a headform cranial portion configured to embrace the human cranium with a headform cranial periphery continuous with the generally cylindrical surface, the recess surface being oriented such that the cylindrical axis is at an angle to the dewar body axis of from about 20 degrees to about 60 degrees,
an array of biomagnetic sensors within the dewar body and positioned around at least a portion of the periphery of the recess surface, and
means for detecting signals produced by the biomagnetic sensors;
positioning a human subject so that a head of the subject is inclined to the horizontal at an angle of the subject of from 0 degrees to 90 degrees;
placing the recess surface of the dewar body over the head of the subject so that the head is received within the recess with the cranium of the head adjacent to the headform cranial portion;
taking biomagnetic data from the subject;
re-positioning the human subject so that the head of the subject is inclined to the horizontal at a second angle of from 0 degrees to 90 degrees, wherein the second angle of the subject is different from the angle of the subject;
changing the angular orientation of the apparatus with respect to the horizontal;
re-placing the recess surface of the dewar body over the head of the subject so that the head of the subject is received within the cylindrical portion of the recess with the cranium of the head adjacent to the headform cranial portion; and
taking biomagnetic data from the subject.

23. A method of measuring biomagnetic signals produced by a human head, comprising the steps of
furnishing an apparatus comprising
an insulated, liquid-tight, elongated hollow dewar body having a dewar body axis parallel to a direction of elongation of the body,
a recess surface in the dewar body, the recess surface being sized sufficiently large to receive a human head therein such that the forehead, cranial, and occipital regions of the head are received therein, the recess having a recess axis parallel to the direction of elongation of the recess, the recess axis being oriented at an angle of from about 20 to about 60 degrees to the dewar body axis,
an array of biomagnetic sensors within the dewar body and positioned around at least a portion of the periphery of the recess surface, and
means for detecting signals produced by the biomagnetic sensors;
positioning a human subject so that a head of the subject is inclined to the horizontal at an angle of the subject of from 0 degrees to 90 degrees;
placing the recess surface of the dewar body over the head of the subject so that the head is received within the recess;
taking biomagnetic data from the subject;
re-positioning the subject so that the head of the subject is inclined to the horizontal at a second angle of the subject of from 0 degrees to 90 degrees, wherein the second angle of the subject is different from the angle of the subject;
changing the angular orientation of the apparatus with respect to the horizontal;
re-placing the recess surface of the dewar body over the head of the subject so that the head of the second subject is received within the recess; and
taking biomagnetic data from the subject.

* * * * *